United States Patent
Zhang et al.

(10) Patent No.: US 8,609,064 B2
(45) Date of Patent: Dec. 17, 2013

(54) NU-85 MOLECULAR SIEVE HAVING A LARGE PORE VOLUME AND PROCESSES FOR PREPARING THE SAME

(75) Inventors: Zhizhi Zhang, Liaoning Province (CN); Xiwen Zhang, Liaoning Province (CN); Bo Qin, Liaoning Province (CN)

(73) Assignees: China Petroleum & Chemical Corporation, Beijing (CN); Fushun Research Institute of Petroleum and Petrochemical, Sinopec, Fushun (CN)

( * ) Notice: Subject to any disclaimer, the term of this patent is extended or adjusted under 35 U.S.C. 154(b) by 220 days.

(21) Appl. No.: 13/271,089

(22) Filed: Oct. 11, 2011

(65) Prior Publication Data

US 2012/0095276 A1    Apr. 19, 2012

(30) Foreign Application Priority Data

Oct. 13, 2010    (CN) .......................... 2010 1 0509203

(51) Int. Cl.
| | |
|---|---|
| *C01B 39/04* | (2006.01) |
| *B01J 29/06* | (2006.01) |
| *B01J 29/80* | (2006.01) |
| *C01B 39/02* | (2006.01) |
| *C07C 5/22* | (2006.01) |
| *C07C 2/66* | (2006.01) |

(52) U.S. Cl.
CPC .............. *C01B 39/023* (2013.01); *C01B 39/04* (2013.01); *B01J 29/06* (2013.01); *B01J 29/80* (2013.01); *C07C 5/222* (2013.01); *C07C 2/66* (2013.01)

USPC .............. 423/700; 423/705; 423/709; 502/60; 208/134; 585/467; 585/481; 585/739

(58) Field of Classification Search
USPC .............. 423/700, 705, 709; 502/60; 208/134; 585/467, 481, 739
See application file for complete search history.

(56) References Cited

U.S. PATENT DOCUMENTS

| | | | | |
|---|---|---|---|---|
| 5,385,718 | A | * | 1/1995 | Casci et al. .................... 423/718 |
| 5,446,234 | A | * | 8/1995 | Casci et al. .................... 585/467 |
| 5,464,799 | A | * | 11/1995 | Casci et al. ...................... 502/65 |
| 6,106,698 | A | | 8/2000 | Benazzi et al. |
| 6,123,914 | A | | 9/2000 | Vaughan et al. |
| 6,153,548 | A | | 11/2000 | Benazzi et al. |
| 6,350,370 | B1 | | 2/2002 | Benazzi et al. |

(Continued)

FOREIGN PATENT DOCUMENTS

| | | |
|---|---|---|
| CN | 1058195 A | 1/1992 |
| CN | 1147422 A | 4/1997 |

(Continued)

OTHER PUBLICATIONS

European Search Report, dated Jan. 30, 2012, for European Patent Application No. EP 11185032.

(Continued)

*Primary Examiner* — David M Brunsman
(74) *Attorney, Agent, or Firm* — Finnegan, Henderson, Farabow, Garrett & Dunner LLP.

(57) ABSTRACT

Disclosed are a novel NU-85 molecular sieve having a specific surface area ranging from about 405 $m^2/g$ to about 470 $m^2/g$ and a pore volume ranging from about 0.27 $cm^3/g$ to about 0.35 $cm^3/g$, and processes for preparing the NU-85 molecular sieve.

12 Claims, 1 Drawing Sheet

(56) References Cited

U.S. PATENT DOCUMENTS

| | | | |
|---|---|---|---|
| 6,471,938 B1 * | 10/2002 | Vaughan et al. | 423/700 |
| 6,784,334 B2 * | 8/2004 | Jolimaitre et al. | 585/820 |
| 2002/0027094 A1 | 3/2002 | Benazzi | |
| 2010/0178241 A1 | 7/2010 | Goergen et al. | |

FOREIGN PATENT DOCUMENTS

| | | |
|---|---|---|
| CN | 1230518 A | 10/1999 |
| CN | 1349960 A | 5/2002 |
| CN | 1362361 A | 8/2002 |
| CN | 101679055 A | 3/2010 |
| CN | 101928008 A | 12/2010 |
| EP | 0 462 745 | 12/1991 |
| FR | 2 765 207 | 12/1998 |
| FR | 2 775 483 | 9/1999 |
| WO | WO 2008/152214 | 12/2008 |

OTHER PUBLICATIONS

Sun et al. "Characterization, catalytic activity and synthetic time optimization of a novel molecular sieve NU-85" *Industrial Catalysis*, vol. 18, No. 9, pp. 34-37, Sep. 2010.

Chen et al., "Advances in research of zeolites with the NES framework topology," *Science & Technology in Chemical Industry*, 17(5): 63-68 (2009).

* cited by examiner

NU-85 MOLECULAR SIEVE HAVING A LARGE PORE VOLUME AND PROCESSES FOR PREPARING THE SAME

This application claims priority under 35 U.S.C. §119 to Chinese Patent Application No. 201010509203.5, filed Oct. 13, 2010.

The present disclosure relates to a novel NU-85 molecular sieve and processes for preparing the same.

NU-85 molecular sieves are a high-silica zeolite molecular sieve having a two-dimensional micropore structure. NU-85 molecular sieves are the intergrowth of EU-1 molecular sieves and NU-87 molecular sieves, and the structural bands of EU-1 molecular sieves and NU-87 molecular sieves therein are interwoven and tightly bound. With such a structure, NU-85 molecular sieves can have the pore channel features and catalytic properties of the two parental molecular sieves, which also enable them to be widely used as the catalyst in the isomerization and alkylation of hydrocarbon compounds.

U.S. Pat. Nos. 5,385,718 and 6,784,334 disclose some NU-85 molecular sieves and the processes for preparing the same.

NU-85 molecular sieves generally have the X-ray diffraction (XRD) characteristic spectral bands shown in the following Table 1.

TABLE 1

The XRD characteristic spectral bands of NU-85 molecular sieves

| Peak No. | 2θ | d | Relative intensity |
|---|---|---|---|
| 1 | 7.96 | 11.09 | Medium |
| 2 | 8.80 | 10.2 | Weak [a] |
| 3 | 19.05 | 4.65 | Medium |
| 4 | 20.56 | 4.31 | 100 |
| 5 | 22.18 | 4.00 | Strong-very strong |
| 6 | 23.27 | 3.81 | Weak-medium |
| 7 | 23.97 | 3.70 | Medium [b] |
| 8 | 25.99 | 3.42 | Weak-medium |
| 9 | 26.53 | 3.35 | Weak-medium [c] |
| 10 | 27.3 | 3.28 | Strong-very strong |

On the basis of such relative intensity gauge, the strongest relative intensity value is defined as 100; "weak" represents a value less than 20; "medium" represents a value of 20-40; "strong" represents a value of 40-60; "very strong" represents a value of more than 60. In the above table, the intensity ratio of the characteristic spectral line marked by "a" to the previous characteristic spectral line is not greater than 0.5; the intensity ratio of the characteristic spectral line marked by "b" to the latter characteristic spectral line is not greater than 1.0; the intensity ratio of the characteristic spectral line marked by "c" to the latter characteristic spectral line is not greater than 1.0.

The NU-85 molecular sieves prepared according to the process in the prior art have a small pore volume ranging generally less than about 0.20 cm$^3$/g, and a small specific surface area ranging generally less than about 400 m$^2$/g.

Disclosed herein is a process for preparing a NU-85 molecular sieve, which can effectively shorten the crystallization time of NU-85 molecular sieves. The resultant NU-85 molecular sieve has a large specific surface area and a large pore volume.

In some embodiments of the disclosure, the NU-85 molecular sieves disclosed herein have a specific surface area ranging from about 405 m$^2$/g to about 470 m$^2$/g, such as from about 410 m$^2$/g to about 460 m$^2$/g, and a pore volume ranging from about 0.27 cm$^3$/g to about 0.35 cm$^3$/g, such as from about 0.28 cm$^3$/g to about 0.32 cm$^3$/g.

The process for preparing the NU-85 molecular sieve disclosed herein comprises formulation of the crystallization material, crystallization, and recovery of the crystallization product, wherein formulation of the crystallization material comprises mixing at least one aluminum source, at least one silicon source, at least one base, at least one template, at least one inorganic salt, at least one EU-1 molecular sieve and water, with a mass ratio of the EU-1 molecular sieve to SiO$_2$ in the at least one silicon source ranging from about 2.5 to about 8.5, such as from about 3.0 to about 7.0.

In some embodiments of the disclosure, the molar ratios of the aluminum source (calculated based on Al$_2$O$_3$), the silicon source (calculated based on SiO$_2$), the base (calculated based on Na$_2$O), the template, the inorganic salt (calculated based on NaL) and water in the crystallization material are:

SiO$_2$/Al$_2$O$_3$=about 30:1 to about 70:1;
R/SiO$_2$=about 0.04:1 to about 0.25:1;
Na$_2$O/SiO$_2$=about 0.05:1 to about 0.3:1;
H$_2$O/SiO$_2$=about 35:1 to about 80:1;
NaL/SiO$_2$=about 0.03:1 to about 0.14:1;

and in some embodiments of the present disclosure:

SiO$_2$/Al$_2$O$_3$=about 40:1 to about 65:1;
R/SiO$_2$=about 0.08:1 to about 0.22:1;
Na$_2$O/SiO$_2$=about 0.1:1 to about 0.2:1;
H$_2$O/SiO$_2$=about 42:1 to about 55:1;
NaL/SiO$_2$=about 0.049:1 to about 0.098:1;

wherein R is a template chosen, for example, from nonamethonium bromide, decamethonium bromide, and undecamethonium bromide. In some embodiments, R is decamethonium bromide. NaL is a sodium salt chosen, for example, from sodium chloride, sodium bromide, sodium nitrate, sodium acetate and sodium oxalate. In some embodiments, NaL is sodium chloride.

Crystallization of the formulated crystallization material disclosed herein comprises dynamic crystallization in two stages comprising: low-temperature crystallization and high-temperatrue crystallization. The low-temperature crystallization comprises high-speed stirring at a stirring rate ranging from about 300 rpm to about 800 rpm and at a crystallization temperature ranging from about 100° C. to about 160° C. for a period of time ranging from about 1 day to about 2 days; then the high-temperature crystallization comprise low-speed stirring at a stirring rate ranging from about 40 rpm to about 250 rpm and at a crystallization temperature ranging from about 170° C. to about 190° C. for a period of time ranging from about 2 days to about 6 days. The entire process of dynamic crystallizion is carried out under autogenous pressure at the crystallization temperatures.

In some embodiments of the disclosure, the at least one aluminum source is chosen from aluminum salts, aluminates, alumina, aluminum hydroxide and alumina sols. In some embodiments, the at least one aluminum source is sodium aluminate. The at least one silicon source is chosen, for example, from white carbon black, silica sol, water glass and tetraethyl orthosilicate. In some embodiments, the at least one silicon source is silica sol. The at least one base used herein comprises, for example, NaOH.

In some embodiments of the disclosure, the SiO$_2$/Al$_2$O$_3$ molar ratio in the at least one EU-1 molecular sieve ranges from about 20 to about 35. The at least one EU-1 molecular sieve may be calcined or non-calcined. In some embodiments, the at least one EU-1 molecular sieve is calcined.

The NU-85 molecular sieve prepared according to the present disclosure can be applied in the fields such as petrochemical industry and can serve as catalytic materials. Such molecular sieves can have good catalytic performance in aromatic alkylation, aromatic isomerization, alkane hydroisomerization, and aromatization of lighter hydrocarbons such as C1-8 alkanes and alkenes.

In the process of the present disclosure, the at least one EU-1 molecular sieve is applied in the formulation of the crystallization material. The at least one EU-1 molecular sieve has a similar structure to that of the NU-85 molecular sieve, and has the features of nano-crystals at the same time. The process of the present disclosure can sufficiently utilize the features of nano-crystals of the EUO-type molecular sieve, to decompose it during the formulation of the crystallization material, and to form a plurality of secondary structural units of the EUO-type molecular sieve, wherein these structural units are also the structural units of the resultant NU-85 molecular sieve. These secondary structural units are used as the directing agent for incorporating silicon and aluminum into the framework of the NU-85 molecular sieve. The process of the present disclosure can effectively shorten the crystallization time of the NU-85 molecular sieves, reduce the preparation cost, and increase the production efficiency. Although nonamethonium bromide, decamethonium bromide, and undecamethonium bromide are not the conventional templates for synthesizing the NU-85 molecular sieves, they can effectively promote the synthesis of the NU-85 molecular sieves by the process of the present disclosure, so as to achieve unexpected technical effects. The present disclosure comprises the two-phase dynamic crystallization, and the resultant product has a larger pore volume and specific surface area.

The NU-85 molecular sieves prepared according to the process of the present disclosure can be used, for example, in C8 aromatic isomerization, toluene disproportionation and trimethylbenzene trans-alkylation, as well as for the preparation of ethyl benzene using benzene and ethylene, with good catalytic effects.

The present disclosure is further illustrated by the following examples, but is not limited by these examples.

EXAMPLES

The specific surface area of the NU-85 molecular sieves of the present disclosure was measured according to the ASTM D3663-2003 method; the pore volume thereof was measured according to the ASTM D4222-2003 method.

Example 1

Formulating solution 1: 2.61 g of $NaAlO_2$, 4.37 g of NaOH, 4.26 g of NaCl and 60.32 g of $DecBr_2$ (decamethonium bromide) were added into 300 ml of $H_2O$, and homogeneously mixed with stirring.

Formulating solution 2: 125 ml of silica sol (containing 45 g of $SiO_2$, the same below) was added into 267 ml of $H_2O$, and homogeneously mixed with stirring.

The solution 2 was added into the solution 1, and homogeneously mixed with stirring. 125 g of EU-1 molecular sieve (prepared according to the process of Example 1 in CN200880017305.6, the same below) was added as crystal seed to prepare a gel.

Figure 1:
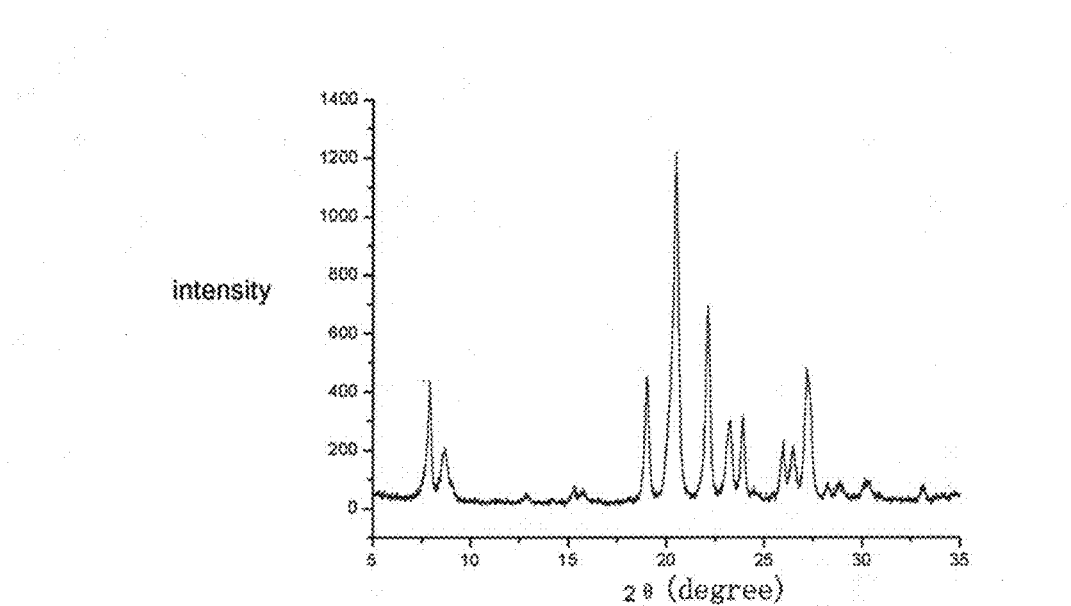
FIG. 1 shows the X-ray diffraction (XRD) patterns of the NU-85 molecular sieve prepared according to Example 1 of the present disclosure.
Figure 2:
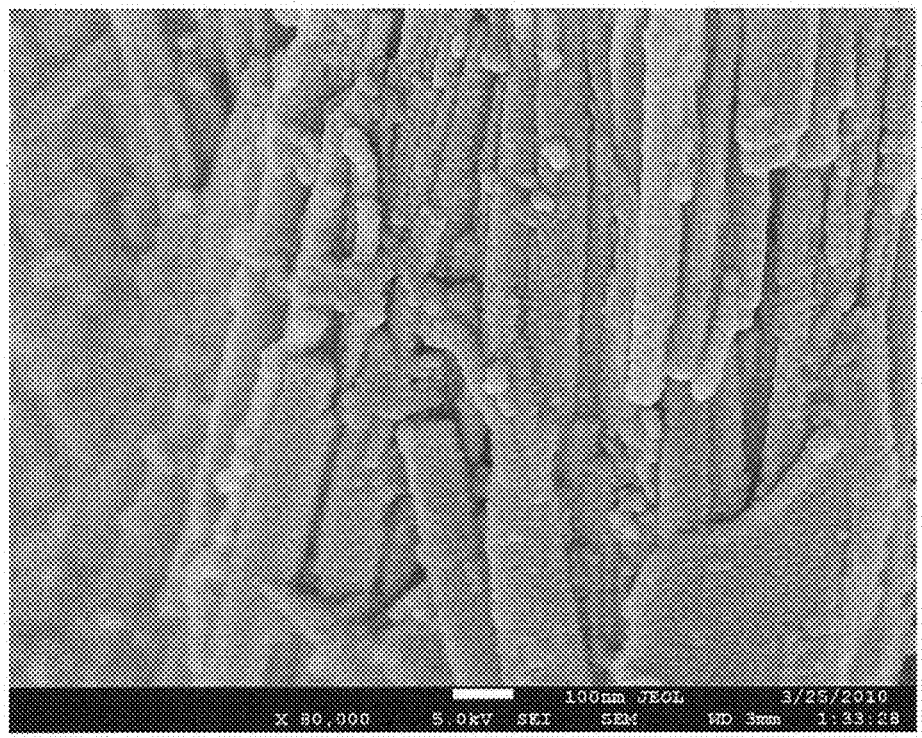
FIG. 2 shows the scanning electron microscope image of the NU-85 molecular sieve prepared according to Example 1 of the present disclosure.

The resultant gel was fed into a 1 L synthesis kettle, crystallized at 100° C. and 450 rpm for 1 day, and then crystallized at 190° C. and 150 rpm for 4 days. Finally, it was cooled down to room temperature, filtered, washed, and dried to obtain the molecular sieve product. Crystalline phase analyses indicated that the product was NU-85 molecular sieves. XRD patterns and the scanning electron microscope image of the product are shown in FIGS. 1 and 2.

The resultant NU-85 molecular sieve had a specific surface area of 405 $m^2/g$, and a pore volume of 0.35 $cm^3/g$.

Example 2

Formulating solution 1: 3.73 g of $NaAlO_2$, 6.48 g of NaOH, 3.82 g of NaCl and 44.67 g of $DecBr_2$ were added into 350 ml of $H_2O$, and homogeneously mixed with stirring.

Formulating solution 2: 125 ml of silica sol was added into 250 ml of $H_2O$, and homogeneously mixed with stirring.

The solution 2 was added into the solution 1, and homogeneously mixed with stirring. 375 g of EU-1 molecular sieve was added as crystal seed to prepare a gel.

The resultant gel was fed into a 1 L synthesis kettle, crystallized at 120° C. and 450 rpm for 1 day, and then crystallized at 180° C. and 100 rpm for 5 days. Finally, it was cooled down to room temperature, filtered, washed, and dried to obtain the molecular sieve product. Crystalline phase analyses indicated that the product was NU-85 molecular sieves.

The resultant NU-85 molecular sieve had a specific surface area of 470 $m^2/g$, and a pore volume of 0.29 $cm^3/g$.

Example 3

Formulating solution 1: 2.98 g of $NaAlO_2$, 8.96 g of NaOH, 3.96 g of NaCl and 55.76 g of $DecBr_2$ were added into 400 ml of $H_2O$, and homogeneously mixed with stirring.

Formulating solution 2: 125 ml of silica sol was added into 342 ml of $H_2O$, and homogeneously mixed with stirring.

The solution 2 was added into the solution 1, and homogeneously mixed with stirring. 268 g of EU-1 molecular sieve was added as crystal seed to prepare a gel.

The resultant gel was fed into a 1 L synthesis kettle, crystallized at 160° C. and 750 rpm for 1 day, and then crystallized at 170° C. and 50 rpm for 4 days. Finally, it was cooled down to room temperature, filtered, washed, and dried to obtain the molecular sieve product. Crystalline phase analyses indicated that the product was NU-85 molecular sieves.

The resultant NU-85 molecular sieve had a specific surface area of 432 $m^2/g$, and a pore volume of 0.31 $cm^3/g$.

Example 4

Formulating solution 1: 3.25 g of $NaAlO_2$, 7.23 g of NaOH, 2.13 g of NaCl and 34.89 g of $DecBr_2$ were added into 350 ml of $H_2O$, and homogeneously mixed with stirring.

Formulating solution 2: 125 ml of silica sol was added into 250 ml of $H_2O$, and homogeneously mixed with stirring.

The solution 2 was added into the solution 1, and homogeneously mixed with stirring. 312 g of EU-1 molecular sieve was added as crystal seed to prepare a gel.

The resultant gel was fed into a 1 L synthesis kettle, crystallized at 140° C. and 650 rpm for 2 days, and then crystallized at 170° C. and 100 rpm for 5 days. Finally, it was cooled down to room temperature, filtered, washed, and dried to obtain the molecular sieve product. Crystalline phase analyses indicated that the product was NU-85 molecular sieves.

The resultant NU-85 molecular sieve had a specific surface area of 428 m$^2$/g, and a pore volume of 0.33 cm$^3$/g.

Example 5

Formulating solution 1: 3.73 g of NaAlO$_2$, 8.98 g of NaOH, 4.02 g of NaCl and 36.54 g of DecBr$_2$ were added into 350 ml of H$_2$O, and homogeneously mixed with stirring.

Formulating solution 2: 125 ml of silica sol was added into 280 ml of H$_2$O, and homogeneously mixed with stirring.

The solution 2 was added into the solution 1, and homogeneously mixed with stirring. 345 g of EU-1 molecular sieve was added as crystal seed to prepare a gel.

The resultant gel was fed into a 1 L synthesis kettle, crystallized at 160° C. and 350 rpm for 1 day, and then crystallized at 190° C. and 150 rpm for 3 days. Finally, it was cooled down to room temperature, filtered, washed, and dried to obtain the molecular sieve product. Crystalline phase analyses indicated that the product was NU-85 molecular sieves.

The resultant NU-85 molecular sieve had a specific surface area of 457 m$^2$/g, and a pore volume of 0.27 cm$^3$/g.

Example 6

Formulating solution 1: 2.89 g of NaAlO$_2$, 6.36 g of NaOH, 3.94 g of NaCl and 69.01 g of DecBr$_2$ were added into 400 ml of H$_2$O, and homogeneously mixed with stirring.

Formulating solution 2: 125 ml of silica sol was added into 250 ml of H$_2$O, and homogeneously mixed with stirring.

The solution 2 was added into the solution 1, and homogeneously mixed with stirring. 335 g of EU-1 molecular sieve was added as crystal seed to prepare a gel.

The resultant gel was fed into a 1 L synthesis kettle, crystallized at 100° C. and 450 rpm for 1 day, and then crystallized at 185° C. and 150 rpm for 4 days. Finally, it was cooled down to room temperature, filtered, washed, and dried to obtain the molecular sieve product. Crystalline phase analyses indicated that the product was NU-85 molecular sieves.

The resultant NU-85 molecular sieve had a specific surface area of 463 m$^2$/g, and a pore volume of 0.28 cm$^3$/g.

Example 7

Formulating solution 1: 2.88 g of NaAlO$_2$, 7.63 g of NaOH, 2.13 g of NaCl and 45.13 g of DecBr$_2$ were added into 350 ml of H$_2$O, and homogeneously mixed with stirring.

Formulating solution 2: 125 ml of silica sol was added into 250 ml of H$_2$O, and homogeneously mixed with stirring.

The solution 2 was added into the solution 1, and homogeneously mixed with stirring. 364 g of EU-1 molecular sieve was added as crystal seed to prepare a gel.

The resultant gel was fed into a 1 L synthesis kettle, crystallized at 140° C. and 750 rpm for 1.5 days, and then crystallized at 175° C. and 150 rpm for 6 days. Finally, it was cooled down to room temperature, filtered, washed, dried to obtain the molecular sieve product. Crystalline phase analyses indicated that the product was NU-85 molecular sieves.

The resultant NU-85 molecular sieve had a specific surface area of 464 m$^2$/g, and a pore volume of 0.29 cm$^3$/g.

Example 8

Formulating solution 1: 4.25 g of NaAlO$_2$, 9.34 g of NaOH, 4.26 g of NaCl and 25.09 g of DecBr$_2$ were added into 400 ml of H$_2$O, and homogeneously mixed with stirring.

Formulating solution 2: 125 ml of silica sol was added into 340 ml of H$_2$O, and homogeneously mixed with stirring.

The solution 2 was added into the solution 1, and homogeneously mixed with stirring. 364 g of EU-1 molecular sieve was added as crystal seed to prepare a gel.

The resultant gel was fed into a 1 L synthesis kettle, crystallized at 100° C. and 300 rpm for 2 days, and then crystallized at 170° C. and 40 rpm for 5 days. Finally, it was cooled down to room temperature, filtered, washed, and dried to obtain the molecular sieve product. Crystalline phase analyses indicated that the product was NU-85 molecular sieves.

The resultant NU-85 molecular sieve had a specific surface area of 453 m$^2$/g, and a pore volume of 0.30 cm$^3$/g.

Example 9

Comparative Example

Formulating solution 1: 6.8 g of NaAlO$_2$, 8.86 g of NaOH, 2.0 g of NaCl and 51.72 g of HexBr$_2$ (hexamethonium bromide) were added into 350 ml of H$_2$O, and homogeneously mixed with stirring.

Formulating solution 2: 143 ml of silica sol was added into 290 ml of H$_2$O, and homogeneously mixed with stirring.

The solution 2 was added into the solution 1 and homogeneously mixed with stirring to prepare a gel having a molar composition of 60 SiO$_2$:1.7 Al$_2$O$_3$:10 Na$_2$O:10 HexBr$_2$: 3000 H$_2$O.

The resultant gel was fed into a 1 L synthesis kettle, crystallized at 160° C. and 350 rpm for 11 days, and cooled down to room temperature. Finally, it was filtered, washed, and dried to obtain the molecular sieve product. Crystalline phase analyses indicated that the product was NU-85 molecular sieves The resultant NU-85 molecular sieve had a specific surface area of 364 m$^2$/g, and a pore volume of 0.19 cm$^3$/g.

Example 10

NU-85 molecular sieves prepared in Example 1 were calcined at 550° C. for 6 h to remove the template. Then the molecular sieves were mixed with 1M of ammonium nitrate solution in a solid to liquid ratio of 50 g/L, to conduct the ammonium exchange twice at 70° C. for 5 h. The mixture was calcined at 550° C. for 6 h to obtain the hydrogen form of NU-85 molecular sieve NUZ-1.

The NU-85 molecular sieves prepared in Example 9 (comparative example) were treated under the same conditions to obtain NUZ-2.

Example 11

Preparation of Cumene from Benzene and Propylene Using NU-85 Molecular Sieves

Cumene was prepared from benzene and propylene by using NUZ-1 and NUZ-2 obtained in Example 10. The reaction conditions were as follows: temperature: 110° C., pressure: 3.0 MPa, propylene volume space velocity: 15.0 h$^{-1}$, and starting material benzene/propylene molar ratio: 4:1. The reaction results were listed in Table 2.

TABLE 2

Results of reaction of benzene with propylene

| Molecular sieves | Conversion rate of propylene % | Selectivity of cumene % |
|---|---|---|
| NUZ-1 | 96.2 | 89.1 |
| NUZ-2 | 90.5 | 81.8 |

Conversion rate of propylene % = (the molar amount of propylene in the feed stream − the molar amount of propylene in the product stream)/the molar amount of propylene in the feed stream*100%;
Selectivity of cumene % = the molar amount of cumene/the molar amount of the converted propylene*100%.

Example 12

C8 Aromatic Isomerization Using NU-85 Molecular Sieves

Alumina, NUZ-1 molecular sieves prepared in Example 10 and an active metal (such as platinum) were mixed, kneaded, and extrusion-molded to prepare a catalyst C1. EU-1 molecular sieves were used to prepare a catalyst C2 as a control. The catalysts contained 30 wt. % of molecular sieves, 0.3 wt. % of platinum as the active metal and 69.7 wt. % of alumina. The reaction materials contained 0.01 mol. % of benzene, 0.13 mol. % of toluene, 12.16 mol. % of ethylbenzene, 0.4 mol. % of p-xylene, 55.23 mol. % of m-xylene, and 22.58 mol. % of o-xylene. The reactions were carried out at a temperature of 395° C., a pressure of 1.0 MPa, a volume space velocity of 4.0 $h^{-1}$, and a hydrogen/hydrocarbon molar ratio of 4:1. The reaction results are listed in Table 3 (mole percentage).

TABLE 3

Results of C8 aromatic isomerization

| Catalysts | PX/ΣX | Loss % of C8 aromatic | Conversion rate of ethylbenzene % |
|---|---|---|---|
| C1 | 23.5 | 1.7 | 22.2 |
| C2 | 23.1 | 3.9 | 19.1 |

PX/ΣX represents p-xylene/xylenes;
Loss % of C8 aromatic = (the molar amount of C8 aromatic in the feed stream − the molar amount of C8 aromatic in the product stream)/the molar amount of C8 aromatic in the feed stream*100%;
Conversion rate of ethylbenzene % = (the molar amount of ethylbenzene in the feed stream − the molar amount of ethylbenzene in the product stream)/the molar amount of ethylbenzene in the feed stream*100%.

Example 13

Toluene Disproprotionation and Trimethylbenzene Trans-Alkylation Using NU-85 Molecular Sieves NUZ-1 molecular sieves prepared in Example 10 were used, and Mordenite (MOR) (prepared according to the process of Example 9 in CN98110736.2) was used as the comparative molecular sieve. The raw materials contained 60 mol % of toluene and 40 mol % of 1,2,4-trimethylbenzene. The reaction conditions were as follows: temperature: 400° C., pressure: 2.4 MPa, volume space velocity: 1.2 $h^{-1}$, and hydrogen/hydrocarbon volume ratio: 13:1. The reaction results are listed in Table 4 (mole percentage).

TABLE 4

Results of toluene disproprotionation and trimethylbenzene trans-alkylation

| Molecular sieves | Conversion rate of toluene % | Conversion rate of Trimethyl-benzene % | Total selectivity of benzene and C8 aromatic % | Selectivity of Xylene % |
|---|---|---|---|---|
| NUZ-1 | 41.5 | 48.3 | 93.8 | 87.5 |
| MOR | 37.8 | 44.6 | 93.1 | 84.4 |

Conversion rate of toluene % = (the molar amount of toluene in the feed stream − the molar amount of toluene in the product stream)/the molar amount of toluene in the feed stream*100%;
Conversion rate of Trimethylbenzene % = (the molar amount of Trimethylbenzene in the feed stream − the molar amount of Trimethylbenzene in the product stream)/the molar amount of Trimethylbenzene in the feed stream*100%;
Total selectivity of benzene and C8 aromatic % = (the molar amount of benzene in the product + the molar amount of C8 aromatic in the product)/(the molar amount of the converted toluene and the converted trimethylbenzene)*100%;
Selectivity of Xylene % = the molar amount of Xylene in the product/(the molar amount of the converted toluene and the converted trimethylbenzene)*100%.

Example 14

Preparation of Ethylbenzene from Benzene and Ethylene Using NU-85 Molecular Sieves NUZ-1 molecular sieves prepared in Example 10 were used, and β zeolites (prepared according to the process of Example 1 in CN01106040.9) were used as the comparative molecular sieves. The reaction conditions were as follows: temperature: 220° C., pressure: 3.5 MPa, ethylene volume space velocity: 2.0 $h^{-1}$, and starting material of benzene/ethylene molar ratio: 12:1. The reaction results are listed in Table 5 (mole percentage).

TABLE 5

Results of reaction of benzene with ethylene

| Molecular sieves | Conversion rate of ethylene % | Selectivity of ethylbenzene % |
|---|---|---|
| NUZ-1 | 56.4 | 95.5 |
| β zeolite | 41.2 | 90.7 |

Conversion rate of ethylene % = (the molar amount of ethylene in the feed stream − the molar amount of ethylene in the product stream)/the molar amount of ethylene in the feed stream*100%;
Selectivity of ethylbenzene % = the molar amount of ethylbenzene/the molar amount of the converted ethylene*100%.

What is claimed is:

1. A NU-85 molecular sieve, having a specific surface area ranging from about 405 $m^2/g$ to about 470 $m^2/g$, and a pore volume ranging from about 0.27 $cm^3/g$ to about 0.35 $cm^3/g$.

2. The NU-85 molecular sieve according to claim 1, having a specific surface area ranging from about 410 $m^2/g$ to about 460 $m^2/g$.

3. The NU-85 molecular sieve according to claim 1, having a pore volume ranging from about 0.28 $cm^3/g$ to about 0.32 $cm^3/g$.

4. A process for preparing a NU-85 molecular sieve, comprising:
mixing at least one aluminum source, at least one silicon source, at least one base, at least one template, at least one inorganic salt, at least one EU-1 molecular sieve and water, wherein the mass ratio of the EU-1 molecular sieve to $SiO_2$ in the silicon source ranges from about 2.5 to about 8.5, and wherein the molar ratios of the aluminum source (calculated based on $Al_2O_3$), the silicon source (calculated based on $SiO_2$), the base (calculated based on $Na_2O$), the template, the inorganic salt (calculated based on NaI) and water range as follows:

$SiO_2/Al_2O_3$=about 30:1 to about 70:1;
$R/SiO_2$=about 0.04:1 to about 0.25:1;
$Na_2O/SiO_2$=about 0.05:1 to about 0.3:1;
$H_2O/SiO_2$=about 35:1 to about 80:1;
$NaL/SiO_2$=about 0.03:1 to about 0.14:1;
  wherein R is the at least one template chosen from nonamethonium bromide, decamethonium bromide, and undecamethonium bromide; NaL is a sodium salt;
and crystallizing the mixture obtained above by dynamic crystallization comprising two stages: low-temperature crystallization and high-temperature crystallization, wherein the low-temperature crystallization comprises high-speed stirring at a stirring rate ranging from about 300 rpm to about 800 rpm and at a crystallization temperature ranging from about 100° C. to about 160° C. for a period of time ranging from about 1 day to about 2 days; then the high-temperature crystallization comprises low-speed stirring at a stirring rate ranging from about 40 rpm to about 250 rpm and at a crystallization temperature ranging from about 170° C. to about 190° C. for a period of time ranging from about 2 days to about 6 days.

5. The process according to claim 4, wherein the molar ratios of the aluminum source, the silicon source, the base, the template, the inorganic salt and water range as follows:
$SiO_2/Al_2O_3$=about 40:1 to about 65:1;
$R/SiO_2$=about 0.08:1 to about 0.22:1;
$Na_2O/SiO_2$=about 0.1:1 to about 0.2:1;
$H_2O/SiO_2$=about 42:1 to about 55:1; and
$NaL/SiO_2$=about 0.0049:1 to about 0.098:1.

6. The process according to claim 4, wherein the mass ratio of the EU-1 molecular sieve to $SiO_2$ in the silicon source ranges from about 3:1 to about 7:1.

7. The process according to claim 4, wherein the entire crystallization procedure is carried out under autogenous pressure at said crystallization temperatures.

8. The process according to claim 4, wherein the sodium salt NaL is chosen from sodium chloride, sodium bromide, sodium nitrate, sodium acetate and sodium oxalate, and mixture thereof.

9. The process according to claim 4, wherein the at least one aluminum source is chosen from aluminum salts, aluminates, alumina, aluminum hydroxide and alumina sols.

10. The process according to claim 4, wherein the at least one silicon source is chosen from white carbon black, silica sol, water glass and tetraethyl orthosilicate.

11. The process according to claim 4, wherein the $SiO_2/Al_2O_3$ molar ratio in the EU-1 molecular sieve ranges from about 20:1 to about 35:1.

12. A process for aromatic alkylation, aromatic isomerization and/or alkane hydroisomerization comprising: adding the NU-85 molecular sieve according to claim 1 in a reaction mixture.

* * * * *